US006407316B1

(12) United States Patent
Holmes et al.

(10) Patent No.: US 6,407,316 B1
(45) Date of Patent: Jun. 18, 2002

(54) METHOD OF INCREASING FOREIGN PROTEIN EXPRESSION

(75) Inventors: Keith A. Holmes, Cary; Daniel D. Stahl, Raleigh, both of NC (US)

(73) Assignee: Rhone-Poulenc AG Company Inc., Research Triangle Park, NC (US)

( * ) Notice: Subject to any disclaimer, the term of this patent is extended or adjusted under 35 U.S.C. 154(b) by 0 days.

(21) Appl. No.: 09/138,027

(22) Filed: Aug. 21, 1998

Related U.S. Application Data

(60) Provisional application No. 60/056,638, filed on Aug. 22, 1997, provisional application No. 60/079,628, filed on Mar. 27, 1998, and provisional application No. 60/084,477, filed on May 6, 1998.

(30) Foreign Application Priority Data

Mar. 27, 1998 (FR) .............................. 98 04067

(51) Int. Cl.$^7$ ................. C12N 15/09; C12N 15/31; C12N 15/82; A01H 5/00
(52) U.S. Cl. .................. 800/302; 800/278; 800/288; 800/295; 800/298; 800/314; 536/23.71; 536/24.1; 435/69.1; 435/440
(58) Field of Search ................ 800/295, 298, 800/278, 288, 302, 314; 435/440, 69.1, 24.1; 536/23.71

(56) References Cited

U.S. PATENT DOCUMENTS 5,352,654 A * 10/1994 Föry et al. ............. 504/230

OTHER PUBLICATIONS

Yadav et al. Ind. J. Plant Protection. 1978. vol.:6(2), pp. 72–75.*

Perlak et al. Biotechnology. 1990. vol. 10:939–943.*

C. Tomlin, ed. (1994) "The Pesticide Manual," 10$^{th}$ edition, British Crop Protection Council, UK, pp 24–26.

* cited by examiner

Primary Examiner—Elizabeth F. McElwain
Assistant Examiner—Medina A. Ibrahim
(74) Attorney, Agent, or Firm—Baker Botts L.L.P.

(57) ABSTRACT

A method of increasing protein expression encoded by a foreign gene in plants which comprises treating a locus comprising the plant or the seed from which it grows with aldicarb. A method of controlling pests at a locus, which locus comprises a plant containing a gene which encodes for Bt endotoxin, the method comprising the application of aldicarb at the plant or at the seed from which it grows. A method of controlling weeds at a locus, which locus comprises a plant containing a foreign gene which encodes a protein imparting tolerance to an herbicide, wherein the herbicide is applied in locus to plant, the method comprising the application of aldicarb to the plant or to the seed from which it grows. A method of increasing the time during which an herbicide may be applied to an herbicide tolerant plant, which method comprises applying a systemic pesticide to the plant or to a seed from which it grows.

11 Claims, No Drawings

METHOD OF INCREASING FOREIGN PROTEIN EXPRESSION

CROSS REFERENCE TO RELATED APPLICATIONS

This application claims priority of provisional applications No. 60/056,638 filed Aug. 22, 1997; No. 60/079,628 filed Mar. 27, 1998; and No. 60/084,477 filed May 6, 1998.

FIELD OF THE INVENTION

The present invention relates to a method of increasing foreign protein expression in plants, a method of controlling insects at a locus, a method of increasing the time during which an herbicide may be applied to a herbicide tolerant plant, a plant in which the expression of a foreign protein has been increased by the application of aldicarb and a method of growing crops.

BACKGROUND OF THE INVENTION

It is known in the field of plant biotechnology that heterologous genes encoding foreign proteins which impart herbicide tolerance, disease resistance or toxicity to insects (insect resistance), or improve the quality of the crops, can be incorporated into the genome of certain plants. These genetically transformed plants can express these proteins for the added protection of the plants, or higher quality of the crops. Genes coding for protein imparting herbicide tolerance are known in the art, including genes imparting tolerance to oxynil herbicides (U.S. Pat. Nos. 4,810,648 and 5,559,024), genes imparting tolerance to glyphosate and EPSPS inhibitor herbicides (U.S. Pat. Nos. 4,535,060, 4,769,061, 5,094,945, 4,940,835, 5,188,642, 4,971,908, 5,145,783, 5,312,910, 5,310,667, 5,633,435, 5,627,061, 5,554,798, 5,633,448, WO 97/04103), genes imparting tolerance to glufosinate (EP 242 236), as well as genes imparting tolerance to HPPD inhibitors (WO 96/38567 and WO 98/02562). Genes coding for proteins imparting disease resistance are known in the art, including lytic peptides, oxalate oxydase genes for tolerance to sclerotinia or chitinases. Genes imparting insect resistance are also known in the art, including genes which encode for *Bacillus thuringiensis* (Bt) endotoxins (Inter alia, U.S. Pat. Nos. 5,460,963, 5,683,691, 5,545,565, 5,530,197, 5,317,096) etc., or for insecticidal toxins isolated from Photorhabdus (WO 97/17432 or WO 98/08932). In general, these heterologous genes have been placed in a variety of plants including cotton.

It is also known that the levels of protein encoded by the heterologous genes in the transgenic plants can vary according to inter alia environmental conditions. For example, the grower of the said plants can be led to believe that the said plants are capable of tolerance to herbicide without being substantially damaged by the herbicide, or capable of resistance to diseases or withstanding attack by insect pests without further assistance from other pesticides. However, it is a severe problem for the grower if the said plants do not express the said protein at the correct time, and in an effective amount, particularly a pesticidally effective amount, more particularly an insecticidally effective amount in case of insect resistance. For example, in the case of Bt endotoxin, if there is not enough in the said plants, then the plants are susceptible to damage from pests, particularly lepidopteran pests, including bollworms. Cotton is such a plant that may be severely affected by bollworm attack. For another example, in the case of cotton seeds or plants comprising a gene encoding a Type II EPSPS, like Roundup Ready® Cotton, the window for application of EPSPS inhibitor herbicides is very strict and narrow (before the 4 leaves stage), and bolls may be damaged when the level of EPSPS expression is not sufficient to impart a proper level of tolerance to glyphosate, leading to an unacceptable loss of yield for the farmer.

Although it is known that aldicarb is a systemically acting insecticide, acaricide and nematicide and generally provide plants with a plant growth promoting effect, aldicarb is not generally effective against lepidopteran species when applied at the seed. Aldicarb is also known as 2-methyl-2-(methylthio)propionaldehyde O-(methylcarbamoyl)oxime.

SUMMARY OF THE INVENTION

An object of the present invention is to enhance the expression of heterologous proteins encoded by genes in plants. Another object of the present invention is to enhance the expression of *Bacillus thuringiensis* endotoxin in plants.

Another object of the present invention is to enhance the expression of proteins imparting herbicide tolerance in plants.

Another object of the present invention is to provide an improved method for the control of pests at a locus.

Another object of the present invention is to provide an improved method of application of an herbicide to a plant tolerant to the said herbicide.

Another object of the invention is to provide an improved plant protected from predacious insects.

Another object of the invention is to provide a plant with improved protection from herbivorous insects.

Another object of the invention is to provide an improved plant comprising a foreign gene which encodes for a foreign protein.

Another object of the invention is to provide an improved seed comprising a foreign gene which encodes for a foreign protein.

These objects are met in whole or in part by the present invention.

DETAILED DESCRIPTION OF THE INVENTION

The present invention relates to a method of increasing foreign protein expression encoded by a foreign gene in plants comprising treating the plant or a seed from which it grows with aldicarb.

By the term "heterologous gene" or "foreign gene" is meant a gene that has been transformed or introduced into the plant, particularly integrated into the transformed plant genome, for example, transformed into the plant or an ancestor thereof, more particularly a gene that is not naturally present in the transformed plant, or even more particularly a gene which contains a sequence coding for a heterologous or foreign protein, including regulatory elements appropriate for controlling the expression of the said coding sequence in the plant cells, for example, promoters, terminators, pre-pro peptides, or transit peptides, the latter driving the expression of the said heterologous protein in a specific targeted region of the plant cell. Promoters controlling the expression of a gene in plant cells are well known in the field of plant biotechnology, including any promoter sequence of a gene naturally expressed in plants or plant cells, form plant, viral or bacterial origin. Suitable such promoters are disclosed in Weising & al (1988, Annual Rev. Genet., 22:241 herein by reference). The following is a partial representative list of promoters suitable for use herein: regulatory sequences from the T-DNA of *A. tumefaciens*, including mannopine synthase, nopaline synthase and octopine synthase; regulatory sequences from plant origin, including alcohol deshydrogenase promoter from corn, light inducible promoters such as ribulose-biscarboxylase/oxygenase small subunit promoters (SSU RuBisCO) from genes of a variety of species and the major chlorophyl a/b binding gene promoters, histone promoters (EP 507 698), actin promoters, maize ubiquitin 1 promoters (Christenses & al., 1996, Transgenic Res., 5:213); regulatory sequences from viral origins, such as 19S or 35S promoters of the cauliflower mosaic virus, (U.S. Pat. Nos. 5,352,605; 5,530,196); developmentally regulated promoters such as waxy, zein, or bronze promoters from maize ; as well as synthetic or other natural promoters which are either inducible or constitutive, including those promoters exhibiting organ specific expression or expression at specific development stage(s) of the plant, like the promoter of napin (EP 255 378) or the alpha-tubulin promoter (U.S. Pat. No. 5,635,618).

By the term "heterologous protein" or "foreign protein" is meant a protein of interest produced by the expression of the foreign gene in the plants. It may be aprotein naturally present in the transformed plant specie but expressed at levels or in specific plant tissues or targeted regions of the plant cells, not naturally occurring in the said transformed plant specie, or a protein not naturally present in the transformed plant specie.

The invention provides a method of increasing foreign gene expression in transgenic plants which method comprises treating the plant or a seed from which it grows with aldicarb.

The transgenic plants according to the invention include cotton, corn, potato, soybean, sunflower, rape seed oil, sugar cane, sugar beet, rice, alfalfa, or banana plants, preferably cotton, corn or potato plants, most preferably a cotton plant.

Preferably, the foreign genes according to the present invention are all the foreign or heterologous genes coding for proteins of interest to impart herbicide tolerance, disease resistance or toxicity to insects (insect resistance), or to improve quality of the crops, known in the art and/or disclosed here above.

As a preferred embodiment of the present invention, the heterologous or foreign gene encodes a protein to impart herbicide tolerance, more preferably tolerance to an oxynil herbicide (disclosed in U.S. Pat. Nos. 4,810,648 and 5,559,024, incorporated herein by reference), to EPSPS inhibitor herbicides, including glyphosate and its various salts (disclosed in U.S. Pat. Nos. 4,535,060, 4,769,061, 5,094,945, 4,940,835, 5,188,642, 4,971,908, 5,145,783, 5,312,910, 5,310,667, 5,633,435, 5,627,061, 5,554,798, 5,633,448, WO 97/04103, incorporated herein by reference), to glufosinate (EP 242 236, incorporated herein by reference), or to HPPD inhibitors (WO 96/38567 and WO 98/02562, incorporated herein by reference). More preferably, the heterologous or foreign gene encodes a protein to impart tolerance to EPSPS inhibitor herbicides.

As another preferred embodiment of the present invention, the heterologous or foreign gene encodes a protein to impart insect resistance, more preferably genes which encode for *Bacillus thuringiensis* (Bt) endotoxins (Inter alia, U.S. Pat. Nos. 5,460,963, 5,683,691, 5,545,565, 5,530,197, 5,317,096, incorporated herein by reference). The genes that are preferably embraced by the instant invention are cryI, cryII, cryIII, and cryIV genes. More preferably, the genes include: cryIA(a), cryIA(b); cryIA(c); and cryIIIA(a). Most preferably the gene is cryIA(a), cryIA(b) or cryM(c). The type of plant which expresses a Bt endotoxin is known as a "Bt" plant, for example "Bt-cotton", "Bt-com" or "Bt-potato."

The promoters controlling the expression of the above genes in plant cells include the following: regulatory sequences from the T-DNA of *A. tumefaciens*, including mannopine synthase, nopaline synthase and octopine synthase; regulatory sequences from plant origin, including alcohol deshydrogenase promoter from corn, light inducible promoters such as ribulose-biscarboxylase/oxygenase small subunit promoters (SSU RuBisCO) from genes of a variety of species and the major chlorophyl a/b binding gene promoters, histone promoters (EP 507 698), actin promoters, maize ubiquitin 1 promoters (Christensen & al., 1996, *Transgenic Res.*, 5:213); regulatory sequences from viral origins, such as 19S or 35S promoters of the cauliflower mosaic virus, (U.S. Pat. Nos. 5,352,605; 5,530,196); developmentally regulated promoters such as waxy, zein, or bronze promoters from maize; as well as synthetic or other natural promoters which are either inducible or constitutive, including those promoters exhibiting organ specific expression or expression at specific development stage(s) of the plant, like the napin promoter (EP 255 378) or the alpha-tubulin promoter (U.S. Pat. No. 5,635,618). As a preferred embodiment, the promoter is selected among the group consisting in the ribulose-biscarboxylase/oxygenase small subunit promoters (SSU RuBisCO) from genes of a variety of species, the histone promoters, the actin promoters, the maize ubiquitin 1 promoters and the 35S promoters of the cauliflower mosaic virus (CaMV 35S), most preferably the CaMV 35S promoter.

The transgenic plant may be a Bt-plant in which the foreign gene expresses Bt-endotoxin and/or an herbicide tolerant plant in which the foreign gene expresses a foreign protein imparting tolerance to the said herbicide.

Preferably the transgenic plants are cotton plants, most preferably NuCotna® 32B or NuCotn® 33B or those comprising a foreign gene which encode the cryIA(a) or cryIA (c) genes, BXN® Cotton comprising a foreign gene which encodes a nitrilase for oxynil tolerance, or Roundup Ready® Cotton comprising a foreign gene which encodes for an EPSPS for glyphosate tolerance.

The foreign gene expression can be elevated in any part of the plant, depending upon the result to be achieved. For herbicide tolerance, the foreign gene should be expressed at high levels in all the parts of the plants, more particularly in the green tissues of the transformed plants, e.g., the leaves and reproductive structures. For insecticidal activity, particularly Bt, or herbicide tolerance, the foreign gene may be expressed preferably in the fruiting parts of the cotton plant, most preferably the squares or bolls and may depend on the exact variety of the plant.

Aldicarb may be applied directly to the plant and/or to the seed and/or to a locus where the plant is growing or is to be grown. By the term "to the seed" is meant on or near the seed.

In one embodiment, aldicarb may be applied to the seed in a seed treatment step before or just after planting. That is, the aldicarb and the seed may be placed in the ground simultaneously or sequentially.

Aldicarb may be applied to the locus before or after planting. The plants may be treated with aldicarb by known methods of application such as side-dressing or in furrow application of granules or liquid; or by drilling.

In one other embodiment, aldicarb may be applied to the locus after planting but before emergence of the plant.

In a preferred aspect of the invention, the seeds are treated after planting with aldicarb at a rate of from 0.01 to 6 kg/ha (kilograms of active ingredient per hectare) preferably from 0.05 to 4 kg/ha more preferably from 0.1 to 1 kg/ha. Generally the amount of aldicarb per 100 meters of crop row is of from 10 to 500 g/100 m (grams per 100 meters), preferably from 20 to 100 g/100 m.

In another preferred embodiment of the invention, the seeds after treatment with aldicarb before planting may comprise from 0.001% w/w to 20% w/w of aldicarb to seed, preferably from 0.05% to 10%, more preferably from 0.1% to 5%.

The present invention also relates to a method of controlling pests at a locus, which locus comprises a plant containing a gene which encodes for Bt endotoxin, the method comprising the application of aldicarb to the plant or to the seed from which it grows.

It has been unexpectedly found that the application of aldicarb to the plant or to the seed from which it grows improves the protection of the plant from attack by pests, preferably insect pests, more preferably of the Orders Lepidoptera, Coleoptera or Diptera. More preferably, the pests are of the family Noctuidae, even more preferably *Heliothis* spp. or *Helicoverpa* spp. Another pest species controlled by the method of the instant invention is *Pectinophora* spp particularly *Pectinophoragossypiella*. Specific pests controlled by the instant invention include at least one of the following species: *Helicoverpa armigera* (also known as *Heliothis armigera*); *Helicoverpa virescens* (also known as *Heliothis virescens* or Tobacco budworm); *Heliothis punctigera*; *Heliothis zea* (cotton bollworm); *Heliothis assulta*; and *Heliothis peltigera*.

Other Lepidoptera that may be controlled by the method of the present invention include *Ostrinia nubilalis, Spodoptera littoralis, Spodoptera exigua, Spodoptera ftugiperda, Manduca sexta, Pieris rapae, Trichoplusia ni,* and *Alabama argillacea*.

Coleoptera that may be controlled by the method of the present invention include the family Crysomelidae, particularly *Leptinotarsa decemlineata* and *Diabrotica undecimpunctata howardi*.

Diptera that may be controlled by the method of the present invention include insects of the family Phorbia, particularly *Phorbia brassicae* and *Phorbia platura*.

The transgenic Bt-plants according to the invention include cotton, corn, potato, sugar cane or rice plants, preferably cotton, corn or potato plants, most preferably a cotton plant.

In a highly preferred aspect of the instant invention, it has been unexpectedly found that in Bt-cotton plants treated with aldicarb, the control of certain species of lepidoptera, most preferably Heliothis armigera, is higher than in those Bt-cotton plants not treated with aldicarb. The Bt-cotton in the instant invention is most commonly known commercially as NuCotn 32B or NuCotn 33B or Ingard.

The present invention also relates to a method of controlling weeds at a locus, which locus comprises a plant containing a foreign gene which encodes a protein imparting tolerance to an herbicide, wherein the said herbicide is applied in said locus to said plant, the method comprising the application of aldicarb to the plant or to the seed from which it grows.

The present invention also relates to a method of increasing the time during which an herbicide may be applied to an herbicide tolerant plant, which method comprises applying a systewmic pesticide to the said plant or to a seed from which it grows or at a locus where the plant is growing or is to be grown.

As a preferred embodiment, the herbicide is an EPSPS inhibitor herbicide, including glyphosate and its various salts, like the isopropylammonium salt or the sulfosate salt (i.e. Roundup® or Touch Down®), and the foreign gene encodes for a protein imparting tolerance to the said EPSPS inhibitor herbicide.

By the term systemic pesticide is meant an pesticide which, when applied to one part of a plant or the seed from which it grows, moves or is moved to another part of the plant. For example, the pesticide may be applied to the roots of a plant and may be moved to the leaves of the plant. In a highly preferred embodiment, the pesticide is phloem-mobile. The pesticide is generally an insecticide, nematicide, fungicide or plant growth regulator, preferably an insecticide or nematicide. The pesticide is generally translocatable and more preferably water soluble at ambient temperature, the water solubility being generally higher than 0.5 g/l, preferably higher than 2 g/l at ambient temperature. The pesticide can be provided in a formulation that is generally translocatable and more preferably water soluable at ambient temperature.

A preferred group of insecticides or nematicides according to the invention are carbamates. Carbamates are a well-known group of pesticides: those skilled in the art will recognize these in *The Pesticide Manual* $10^{th}$ ed., edited by C. Tomlin, British Corp Protection Council, United Kingdom, 1994 or later editions thereof or in other references known to those skilled in the art. A preferred group of carbamates are N-methyl carbamates, that is those substances that possess the substituent —OC(O)NHMe. A particulary preferred carbamate that can be used according to the instant invention is 2-methyl-2(methylthio) propionaldehyde O-methylcarbamoyloxime (aldicarb). Other carbamates that can be used according to the invention are 2,3-dihydro-2,2-dimethylbenzofuran-7-yl methylcarbamate (carbofuran) and N,N-dimethyl-2-methylcarbamoyloxyimino-2-(methylthio)aceetamide (oxamyl). A carbamate can be used alone or in combination with other pesticides.

Other insecticides or nematicides that can be used according to the instant invention either alone or in combination with other pesticides include: nitromethylenes or nitroimines including 1-(6-chloro-3-pyridylmethyl)-N-nitroimidazolidin-2-ylideneamine (imidacloprid) or a metabolite thereof; or thiamethoxam; or a cyanoimine which is active at the nicotinic acid pathway; organophosphates including disulfoton (which is also known by the trademark Disyston) or phorate (which is known by the trademark Thimet).

Use rates, methods of treatment and formulations of the above substances are known to those skilled in the art. For example, in a preferred embodiment, seeds are treated after planting with aldicarb at from 0.01 to 6 kg/ha, preferably from 0.05 to 4 kg/ha, and more preferably from 0.1 to 1 kg/ha. In another example, seeds are treated with aldicarb before planting at 0.001% w/w to 20% w/w of aldicarb to seed, preferably from 0.05% w/w to 10% w/w of aldicarb to seed, and more preferably from 0.1% w/w to 5% w/w aldicarb to seed. In another example, seeds are treated after planting with disulfoton at from 1 to 50 kg/ha, preferably from 10 to 30 kg/ha, and more preferably from 20 to 25 kg/ha. In another example, seeds are treated before planting with imidocloprid at from 0.01 to 1.0 kg/100 kg seed, and preferably at from 0.1 to 0.5 kg/100 kg of seed.

A particularly preferred pesticide which is used in the present invention is aldicarb. In fact, although the pesticides above may be used in the present invention, aldicarb allows the continued early fruiting of the plant despite the late application of glyphosate.

It has been unexpectedly found that the application of a systemic pesticide not only increases the tolerance to the herbicide of the transgenic plant, but also increase the time during which the glyphosate may be applied in said locus to said plant (glyphosate being understood as the representative of the whole familly of EPSPS inhibitor herbicides).

The transgenic herbicide tolerant plants according to the invention include cotton, corn, soybean, sunflower, rape seed oil, sugar cane, sugar beet or alfalfa plants, preferably cotton, corn or soybean plants, most preferably a cotton plant.

The number of applications of EPSPS inhibitor herbicides, including glyphosate or a salt thereof, per growing season may also be increased, in general from 1 to 7 sprays per season, preferably 2 to 6 sprays per season, more preferably 2 to 5 sprays per season.

In the case of cotton, glyphosate or a salt thereof may be applied on the plant from the emergence of the plant to harvest of the cotton, preferably from emergence to boll opening, more preferably from emergence to the 12 leaf stage, even more preferably from emergence to the 8 leaf stage, even more preferably from emergence to the 6 leaf stage.

The present invention also relates to a new composition which comprises aldicarb and a seed containing a foreign gene which encodes for a foreign protein. The foreign gene and the seeds of the plant may be one of those disclosed above. The composition may comprise from 0.001% w/w to 20% w/w of aldicarb to seed, preferably from 0.05% to 10%, more preferably from 0.1% to 5%. The aldicarb may coat the seed in a conventional manner as known to the skilled addressee in the art of seed coatings. In addition, the aldicarb may be injected into the seed before planting.

The present invention also relates to a plant which comprises a foreign gene which encodes for a foreign protein as disclosed here above which has been treated by aldicarb, the said plant having an improved amount of foreign protein.

In the case of insect tolerance and Bt endotoxin, the plant preferably has more endotoxin in the fruiting parts of the plant than in the leaves; in the case of cotton, in the bolls and squares than in the leaves.

Aldicarb, its uses and formulations are described inter alia in *The Pesticide Manual,* 106 edition, Crop Protection Publications, ed. C. Tomlin, Bath, United Kingdom and *Crop Protection Reference* 11th edition, CPR Press, New York, N.Y., USA, 1995. Plants and descriptions of plants that express *Bacillus thuringiensis* delta endotoxin are available from the Monsantog® and Novartis® agrochemical companies. Plants and description of plants that express genes imparting tolerance to an EPSPS inhibitor herbicide are available from the Monsanto® agrochemical company. Salts of glyphosate are available from the Monsanto® and Zeneca® agrochemical companies.

The following examples illustrate the invention.

EXAMPLE 1

Seeds of NuCotn® 32B are planted in a field. Aldicarb, in the form of the commercial product Temik® 15G (a 15% weight/weight granular formulation) is applied in the furrow that comprises the seed at a rate of about 0.5 kg/ha of active ingredient or 3.3 kg/ha of commercial product. At various points in the growing season, the plant tissues are tested for the levels of the delta-endotoxin. The tissues from the plants treated by aldicarb display a higher level of the endotoxin than the tissues from plants not treated by aldicarb.

EXAMPLE 2

Seeds of NuCotn® 32B are planted in a field. Aldicarb, in the form of the commercial product Temik® 15G (a 15% weight/weight granular formulation) is applied as a sidedress at 7.8 kg/ha of commercial product. After a full growing season, there are a larger number of bolls on the plants that have been treated with aldicarb in comparison to those not treated with aldicarb. The amount of damage due to bollworm attack on the cotton is less in those treated with aldicarb in comparison to those not treated with aldicarb.

EXAMPLE 3

Cotton leaves and squares were collected from treatments of Bt Cotton wherein the cotton was treated with Temik® 15G under the following conditions;

A) 0.45 lbs active ingredient per acre at plant (0.5 kg/ha)

B) 0.75 lbs active ingredient per acre at plant; (0.5 kg/ha) and

C) 0.75 lbs active ingredient per acre (0.84 kg/ha) at plant and followed 3 weeks later by a side-dress treatment of 1.0 lbs per acre (1.12 kg/ha) of active ingredient.

One planting was not treated with aldicarb.

After 90 days leaves and squares were collected, washed with soap and water, allowed to dry, washed with acetone, allowed to dry and finally washed with chloroform. The tissues were then freeze dried, ground in a mortar and pestle and stored at room temperature.

The cotton tissues were incorporated into a Heliothis diet and fed to *Heliothis virescens.* The larvae in the cups were weighed at seven days after infestation and the number of pupae were counted 14 and 21 days after infestation. The percent pupation was calculated at the different concentrations and the $EC_{50P}$ (the amount of tissue per liter of diet that reduced pupation by 50%) was calculated for each insecticide treatment to express the amount of toxin activity in the treatment.

At the reading two weeks after infestation, the diet containing leaf tissue of cotton plants treated with aldicarb at plant required higher amounts of tissue to reduce pupation by 50% compared to the untreated check, but the diet containing square tissue required lesser amounts of tissue to reduce pupation by 50%.

At the reading three weeks after infestation, the diet containing leaf tissue of cotton plants treated with aldicarb at plant required higher amounts of tissue to reduce pupation by 50% compared to the untreated check, but the diet containing square tissue required lesser amounts of tissue to reduce pupation by 50%.

This indicates that the Bt endotoxin is at least preferably accumulating more in the squares of the Bt cotton plant when treated with aldicarb.

EXAMPLE 4

V2 INGARD Cotton was treated with a Temik® 15G at plant at a rate of 5 kg per hectare of commercial product. After 3 weeks leaves from the $3^{rd}$ node were picked and fed to *Heliothis annigera* $1^{st}$ instar larvae. At this time the cotton leaves from the third node in the treated plants were less effective than the leaves from the untreated plants.

Two weeks later leaves from the $3^{rd}$ node and $7^{th}$ node were taken from treated and untreated plants. Squares were also sampled. When fed to *Heliothis armigera* larvae, there was a higher mortality in the Temik-treated plant tissue than for the untreated plant tissue. Furthermore, the surviving larvae were significantly smaller when fed the treated leaves than the untreated leaves.

EXAMPLE 5

A plot of Roundup Ready® Cotton (RRC was grown up. One part of the plot was treated with Temik® at a rate of 5.6 kg/ha of commercial product at the time of planting of the seed. Another part was treated with Disyston® (disulfoton) at 22.24 kg of commercial product/ha the time of planting of the seed. Another part of the plot was grown from seed treated with Gauch® (imidactoprid) at a rate of 0.357 kg of commercial product per 100 kg of seed. One part of the plot was left untreated by an insecticide which is called hereafter the untreated check (UTC).

The isopropylamine salt of glyphosate was applied to all the cotton plants at the four-leaf stage in the form of the commercial product Roundup® at a rate of 32 oz of commercial product per acre (=0.17 kg/ha of active ingredient). The following results were observed 45 days after the Roundup® treatment:

| Treatment | Squares per Plant | % change from UTC |
|---|---|---|
| RRC (UTC) | 7.45 | — |
| RRC + aldicarb | 9.05 | +21 |
| RRC + disulfoton | 7.65 | +2 |
| RRC + imidacloprid | 8.70 | +18 |

After 62 days, many squares had matured to bolls and the following observations were made:

| Treatment | Squares + Bolls | % change from UTC |
|---|---|---|
| RRC | 15.1 | — |
| RRC + aldicarb | 18.7 | +18.7 |
| RRC + disulfoton | 12.8 | −15.0 |
| RRC + imidacloprid | 14.8 | −0.2 |

EXAMPLE 6

Roundup Ready® Cotton was grown up as in Example 5 and treated with Roundup at the six-leaf stage.

The following results were observed 40 days after the Roundup® treatment:

| Treatment | Squares per Plant | % change from UTC |
|---|---|---|
| RRC (UTC) | 8.85 | — |
| RRC + aldicarb | 10.95 | +23% |
| RRC + disulfoton | 5.65 | −36% |
| RRC + imidacloprid | 7.60 | −14% |

After 57 days, many of the square had matured to bolls. The following observations were made:

| Treatment | Square & Bolls | % change from UTC |
|---|---|---|
| RRC (UTC) | 14.4 | — |
| RRC + aldicarb | 16.0 | +11 |
| RRC + disulfoton | 16.5 | +14 |
| RRC + imidacloprid | 16.5 | +14 |

The observations set forth in the first tables of Examples 5 and 6 were made on the same day. The observations set forth in the second tables of Examples 5 and 6 were made on the same day.

The results of Example 5 show that for herbicide-tolerant plants treated with herbicide at the four-leaf stage, treatment with aldicarb increases the yield of cotton compared with UTC or cotton treated with other pesticides. The results from Example 6 show that treatment with systemic pesticides increases the time during which glyphosate may be applied without damage to the plant to after the four-leaf stage, and further that for plants treated with herbicide at the six-leaf stage, treatment of seeds of herbicide tolerant plants with systemic pesticides results in higher yields relative to UTC.

All references cited herein are incorporated herein in their entirety.

We claim:

1. A method of increasing the expression of *Bacillus thuringiensis* endotoxin encoded by a foreign polynucleotide in a cotton plant comprising treating a cotton plant that expresses *Bacillus thuringiensis* endotoxin or a seed from which the plant grows with aldicarb, wherein the expression of *Bacillus thuringiensis* endotoxin in said cotton plant treated with aldicarb is increased as compared with untreated cotton plants that express *Bacillus thuringiensis* endotoxin.

2. The method according to claim 1, wherein the foreign polynucleotide is selected among the group consisting of cryI, cryII, cryIII, and cryIV polynucleotides.

3. The method according to claim 2, wherein the foreign polynucleotide is selected among the group consisting of cryIA(a); cryIA(b); cryIA(c); and cryIIIA(a) polynucleotides.

4. The method according to claim 1, wherein the expression of the foreign ploynucleotide is controlled by a promoter selected from the group consisting of the ribulose-biscarboxylase/oxygenase small subunit promoters (SSU RuBisCO), the histone promoters, the actin promoters, the maize ubiquitin 1 promoters and the 35S promoters of the cauliflower mosaic virus (CaMV 35S).

5. The method according to claim 4, wherein the promoter is the CaMV 35S promoter.

6. The method according to claim 1, wherein aldicarb is applied directly to the plant and/or to the seed or to a locus where the plant is growing or is to be grown.

7. The method as claimed in claim 6, wherein aldicarb is applied to the seed in a seed treatment step before or just after planting.

8. The method according to claim 6, wherein aldicarb is applied to the ground before or after planting.

9. The method as claimed in claim 8, wherein aldicarb is applied at the ground after planting but before emergence of the plant.

10. The method as claimed in claim 1, wherein the seeds are treated after planting with aldicarb at a rate of from 0.01 to 6 kg/ha (kilograms of active ingredient per hectare).

11. The method as claimed in claim 1, wherein the seeds after treatment with aldicarb, before planting comprise from 0.001% w/w to 20% w/w of aldicarb to seed.

* * * * *

UNITED STATES PATENT AND TRADEMARK OFFICE
CERTIFICATE OF CORRECTION

PATENT NO. : 6,407,316 B1
DATED : June 18, 2002
INVENTOR(S) : Holmes et al.

It is certified that error appears in the above-identified patent and that said Letters Patent is hereby corrected as shown below:

Column 3,
Line 9, please replace the term "chlorophyl" with the term -- chlorophyll --
Line 24, please replace the term "aprotein" with the term -- a protein --

Column 5,
Line 38, please replace the term "*ftugiperda*" with the term -- *frugiperda* --

Column 6,
Line 2, please replace the term "systewmic" with the term -- systemic --
Line 11, please replace the term "an" with the term -- a --
Line 24, please replace the term "soluable" with the term -- soluble --
Line 35, please replace the term "ticulary" with the term -- ticularly --
Line 41, please replace the term "aceetamide" with the term -- acetamide --

Column 7,
Line 13, please replace the term "familly" with the term -- family --

Column 10,
Line 42, please replace the term "ploynucleotide" with the term -- polynucleotide --
Line 51, please replace the term "and/or" with the term -- or --
Line 58, please replace the term "at" with the term -- to --

Signed and Sealed this

Nineteenth Day of November, 2002

*Attest:*

*Attesting Officer*

JAMES E. ROGAN
*Director of the United States Patent and Trademark Office*